(12) United States Patent
Daamen et al.

(10) Patent No.: US 9,070,695 B2
(45) Date of Patent: Jun. 30, 2015

(54) INTEGRATED CIRCUIT WITH SENSOR AND METHOD OF MANUFACTURING SUCH AN INTEGRATED CIRCUIT

(75) Inventors: Roel Daamen, Herkenbosch (NL); Hendrik Bouman, Nijmegen (NL); Coenraad Cornelis Tak, Waalre (NL)

(73) Assignee: NXP, B.V., Eindhoven (NL)

( * ) Notice: Subject to any disclaimer, the term of this patent is extended or adjusted under 35 U.S.C. 154(b) by 99 days.

(21) Appl. No.: 13/610,692

(22) Filed: Sep. 11, 2012

(65) Prior Publication Data
US 2013/0069176 A1 Mar. 21, 2013

(30) Foreign Application Priority Data
Sep. 21, 2011 (EP) ..................................... 11182122

(51) Int. Cl.
| H01L 27/14 | (2006.01) |
| H01L 23/00 | (2006.01) |
| H01L 23/31 | (2006.01) |
| H01L 21/56 | (2006.01) |
| G01N 27/12 | (2006.01) |
| G01D 11/24 | (2006.01) |

(52) U.S. Cl.
CPC ............ *H01L 23/564* (2013.01); *H01L 23/315* (2013.01); *H01L 23/3157* (2013.01); *H01L 21/565* (2013.01); *G01N 27/121* (2013.01); *G01D 11/245* (2013.01); *H01L 2224/48091* (2013.01); *H01L 2224/48247* (2013.01); *H01L 2224/48465* (2013.01); *H01L 2924/1815* (2013.01); *H01L 2924/3025* (2013.01)

(58) Field of Classification Search
CPC ........ H01L 23/528; H01L 23/31; H01L 23/48
USPC .................... 438/48, 113; 257/E21.599, 414
See application file for complete search history.

(56) References Cited

U.S. PATENT DOCUMENTS

| 4,697,203 | A * | 9/1987 | Sakai et al. ................... 257/681 |
| 5,897,338 | A * | 4/1999 | Kaldenberg ................. 438/116 |
| 6,379,988 | B1 * | 4/2002 | Peterson et al. ............... 438/51 |
| 6,395,585 | B2 * | 5/2002 | Brandl .......................... 438/127 |
| 6,489,178 | B2 * | 12/2002 | Coyle et al. ...................... 438/51 |
| 6,690,569 | B1 | 2/2004 | Mayer et al. |
| 7,109,574 | B2 * | 9/2006 | Chiu et al. .................... 257/684 |
| 7,304,362 | B2 * | 12/2007 | Zhou et al. .................... 257/433 |
| 7,312,106 | B2 * | 12/2007 | Raben ........................... 438/112 |
| 7,901,971 | B2 * | 3/2011 | Hunziker et al. ............... 438/55 |
| 2001/0023087 | A1 * | 9/2001 | Brandl .......................... 438/106 |
| 2006/0260107 | A1 | 11/2006 | Itakura et al. |
| 2007/0222041 | A1 * | 9/2007 | Weng et al. ................... 257/666 |
| 2008/0258318 | A1 * | 10/2008 | Kimura .......................... 257/793 |

(Continued)

OTHER PUBLICATIONS

Boschman Technologies "High Volume Encapsulation, Mems Sensor Chips with Film Assisted Molding", Netherlands MicroNano Conference, 25 pgs. (2008).

(Continued)

*Primary Examiner* — Caleb Henry

(57) ABSTRACT

An integrated circuit package for an integrated circuit having one or more sensor elements in a sensor element area of the circuit. An encapsulation covers bond wires but leaves an opening over the sensor element area. A protection layer is provided over the integrated circuit over which the encapsulation extends, and it has a channel around the sensor element area to act as a trap for any encapsulation material which has crept into the opening area.

14 Claims, 7 Drawing Sheets

(56) References Cited

U.S. PATENT DOCUMENTS

Figure 1:
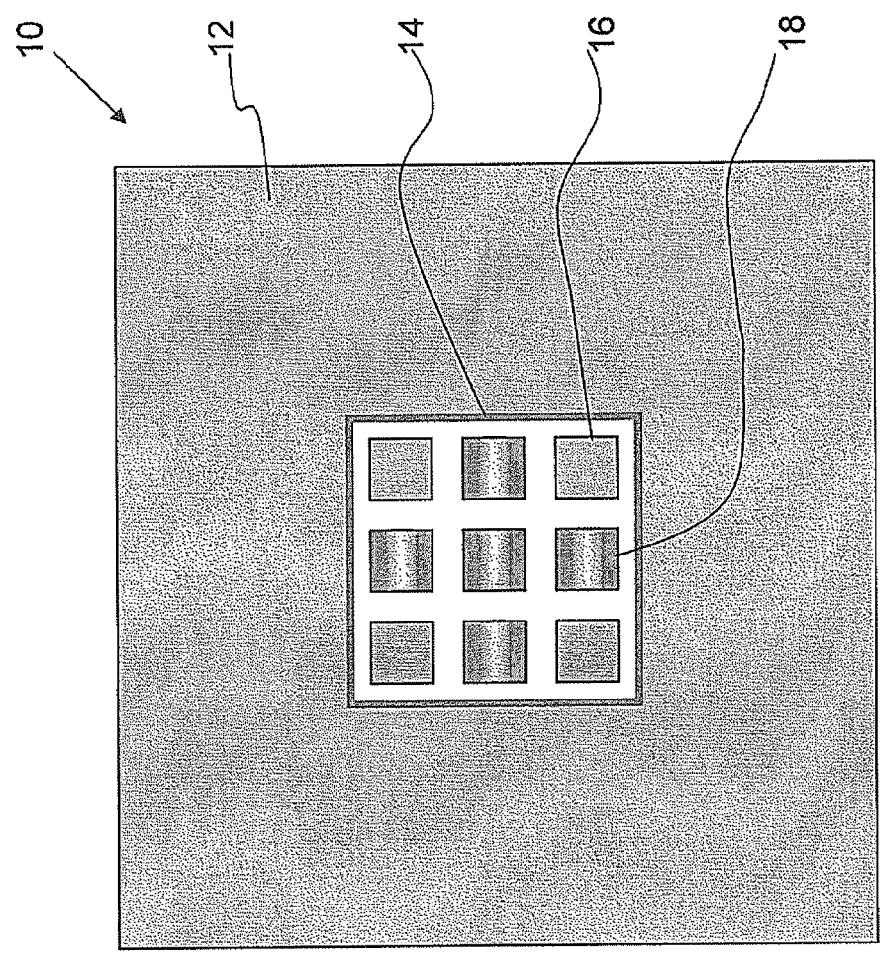

| | | |
|---|---|---|
| 2009/0051052 A1* | 2/2009 | Yoshioka et al. ............. 257/788 |
| 2009/0243015 A1* | 10/2009 | Yoneda et al. ................ 257/434 |
| 2010/0035373 A1* | 2/2010 | Hunziker et al. ............... 438/48 |
| 2010/0117185 A1* | 5/2010 | Hunziker et al. ............. 257/467 |
| 2010/0213607 A1* | 8/2010 | Smeys et al. .................. 257/723 |
| 2010/0230766 A1* | 9/2010 | Elian et al. .................... 257/414 |
| 2012/0126344 A1* | 5/2012 | Elian et al. .................... 257/415 |
| 2012/0211845 A1 | 8/2012 | Daamen et al. |
| 2013/0056703 A1* | 3/2013 | Elian et al. ........................ 257/9 |

OTHER PUBLICATIONS

Extended European Search Report for European Patent Appln. No. 11182122.9 (May 7, 2012).

* cited by examiner

INTEGRATED CIRCUIT WITH SENSOR AND METHOD OF MANUFACTURING SUCH AN INTEGRATED CIRCUIT

CROSS-REFERENCE TO RELATED APPLICATIONS

This application claims the priority under 35 U.S.C. §119 of European patent application no. 11182122.9, filed on Sep. 21, 2011, the contents of which are incorporated by reference herein.

The present invention relates to an integrated circuit (IC) package comprising a substrate carrying one or more sensor elements, and which is connected to bond pads with encapsulated leads. The present invention further relates to a method of manufacturing such an IC package.

Integrated circuits (ICs) can comprise moisture-sensitive sensors, such as relative humidity (RH) sensors or liquid immersion detection sensors. Such sensors may be included in the IC design for a number of reasons.

For instance, such a sensor may be included in the IC to determine whether a malfunctioning IC that has been returned, e.g. to its manufacturer, has been damaged by exposure to moisture, e.g. an immersion event. The determination of such external influences as a cause of malfunction may be of crucial importance to deciding whether or not the customer returning the IC or an electronic device including the IC is entitled to a warranty claim on the device, as misuse such as the aforementioned immersion event typically invalidates the warranty.

Alternatively, such a sensor may be part of the functionality of an IC. There is for instance a trend towards providing near-field communication ICs such as radio-frequency (RF) identification (ID) chips with a range of sensors, such as temperature sensors, ambient light sensors, mechanical shock sensors, liquid immersion sensors, humidity sensors, $CO_2$ sensors, $O_2$ sensors, pH sensors and ethylene sensors, which for instance may be used to monitor the ambient conditions of a product tagged with the chip such that product quality control can be achieved by monitoring the sensor readings of the chip.

In general, a semiconductor device can be formed as a package by attaching the die to a lead frame, with bond wires extending between bond pads of the IC and pads of the lead frame. These bond wires are then encapsulated in a molding compound.

A problem arises when the die comprises sensor elements that must be in contact with the external environment, in that the encapsulation must not cover these sensors. This results in a more complicated packaging process and gives rise to various processing issues.

Many sensor ICs are formed on a single wafer, and after sensor formation, the substrate is subjected to grinding to reduce the thickness of the end product. This takes place before the individual sensor ICs are diced from the wafer and then encapsulated. This grinding process can lead to mechanical damage or contamination of the sensors, particularly as they project above the IC surface.

To form an encapsulation with an open cavity, rubber inserts during transfer molding are conventionally used. Also a so called "film assisted molding" can be used. This involves placing a mold over the IC, which has a central area surrounded by a seal which contacts the top surface of the IC. This seal is made by applying pressure to the mold, and the mold is for example coated with a Teflon film. The mold compound is applied around the outside of the seal, and is not supposed to penetrate the seal line. However, to provide a good seal and prevent molding compound flashing into the open cavity, a high pressure has to be applied, such as 120 bar. These mechanical stresses can lead to die breakage, but if the pressure is reduced mold flashing can be formed in the open cavity area.

According to the present invention, there is provided an integrated circuit package, comprising:
an integrated circuit having at least one sensor element in a sensor element area of the circuit;
a carrier on which the integrated circuit is mounted;
bond wires between the integrated circuit and the carrier;
an encapsulation which covers the bond wires but leaves an opening over the sensor element area,
wherein a protection layer is provided over the integrated circuit over which the encapsulation extends, wherein the protection layer comprises a channel around the sensor element area, which lies inside the opening of the encapsulation.

The channel around the sensor element area acts as a trap for any mold flashing that creeps into the opening area. In this way, the mold pressure can be relaxed. By providing the protection layer beneath the encapsulation (rather than only over the sensor elements), the protection layer also increases the mechanical strength of the IC. For example, the protection layer can be applied before substrate grinding and dicing steps, so that the strength is improved during these steps.

The channel preferably extends fully through the protection layer and comprises a closed shape surrounding the sensor element area.

The protection layer can cover at least one of the sensor elements. Each sensor element which is covered by the protection layer can comprise a protection layer pad over the sensor element surrounded by a pad channel. This pad channel provides isolation of individual sensors, so that any contamination suffered by one sensor element is not transmitted to the other sensor elements through the protection layer. The pad channel can also extend fully through the protection layer.

The protection layer can comprise polyimide, and can be provided over a humidity sensor. The polyimide material might also act as the moisture sensitive material. It can also be provided over a light sensor, and can either be transparent to the light of interest, or it can perform a filtering function.

The sensor elements can comprise ambient light sensors, humidity sensors among others.

The invention also provides a method of forming an integrated circuit package, comprising:
providing an integrated circuit having at least one sensor element in a sensor element area at a top surface of the circuit;
mounting the integrated circuit on a carrier;
forming bond wires between the integrated circuit and the carrier;
forming an encapsulation layer to cover the bond wires but leave an opening over the sensor element area,
wherein the method comprises forming a protection layer over the integrated circuit before mounting on the carrier, and forming a channel in the protection layer around the sensor element area,
and wherein forming the encapsulation layer comprises molding the encapsulation layer up to a barrier formed as part of the mold, with the channel on the inner side of the barrier.

The encapsulation layer molding can be performed by film assisted molding.

Figure 2:
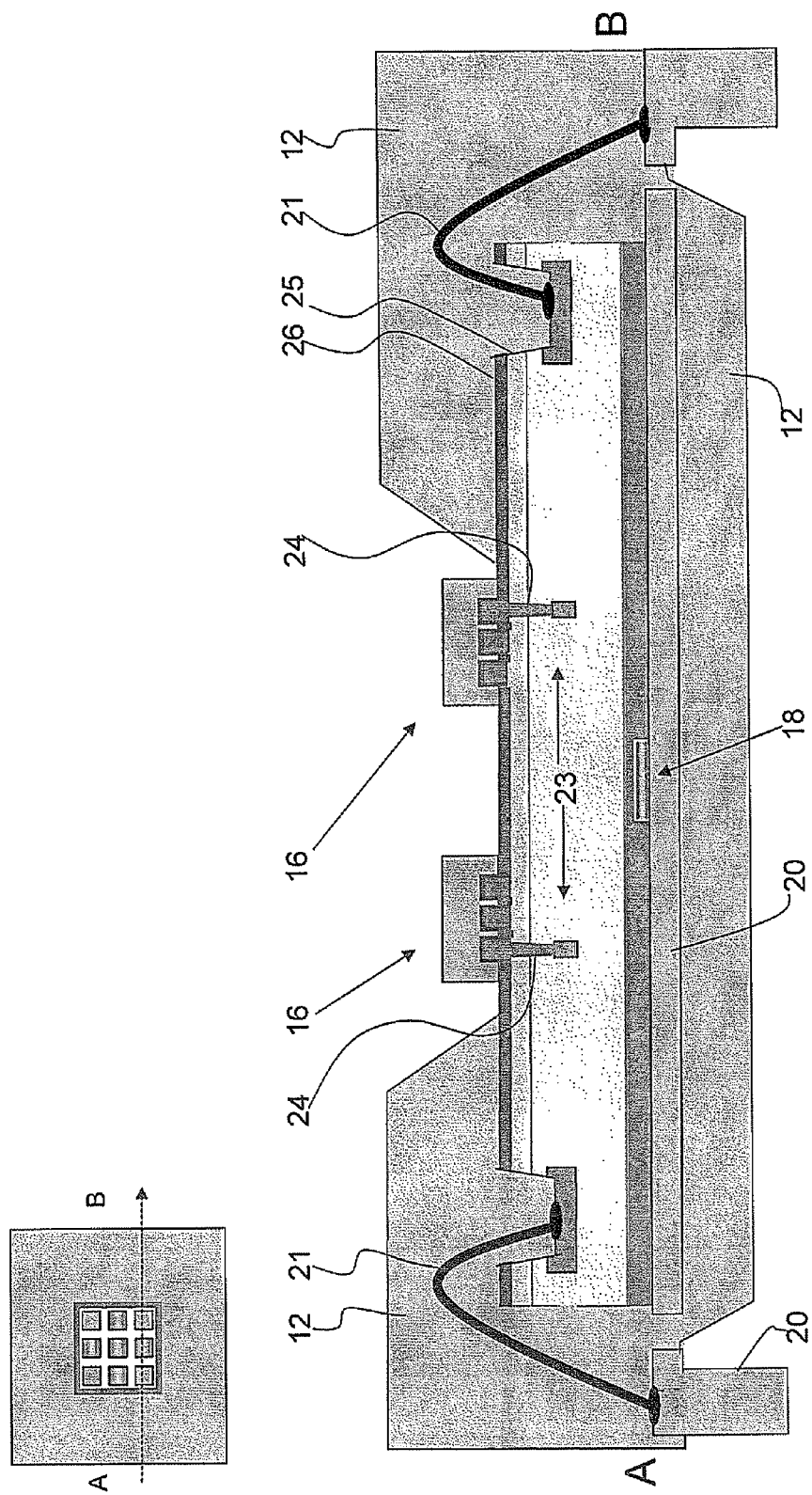
Figure 3:
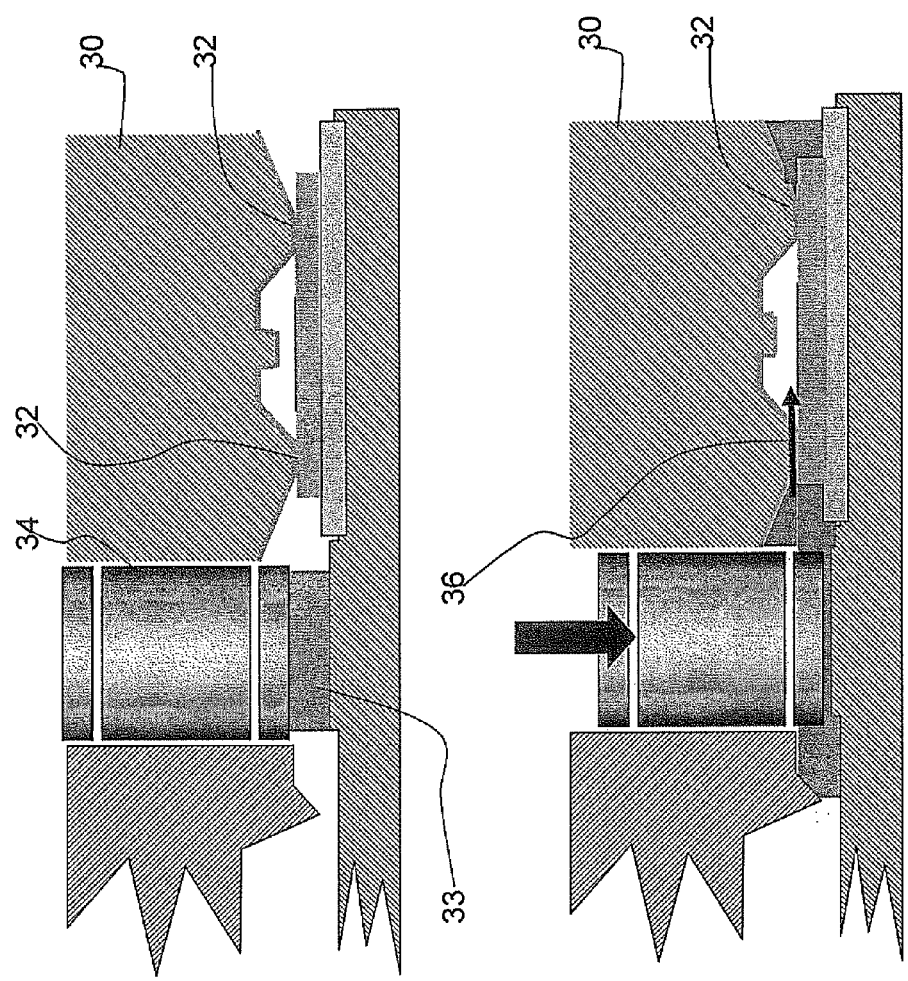
Figure 4:
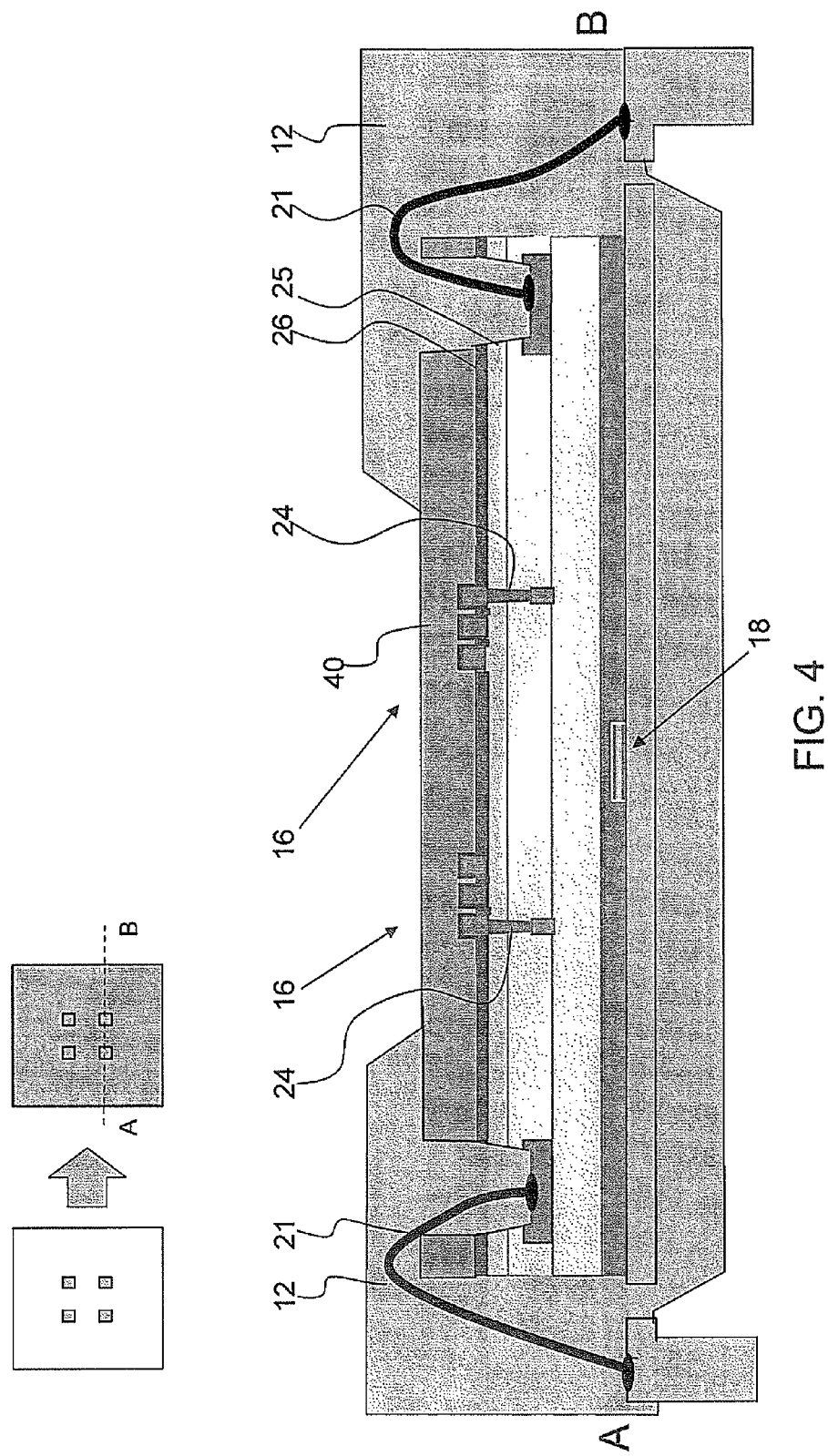
Figure 5:
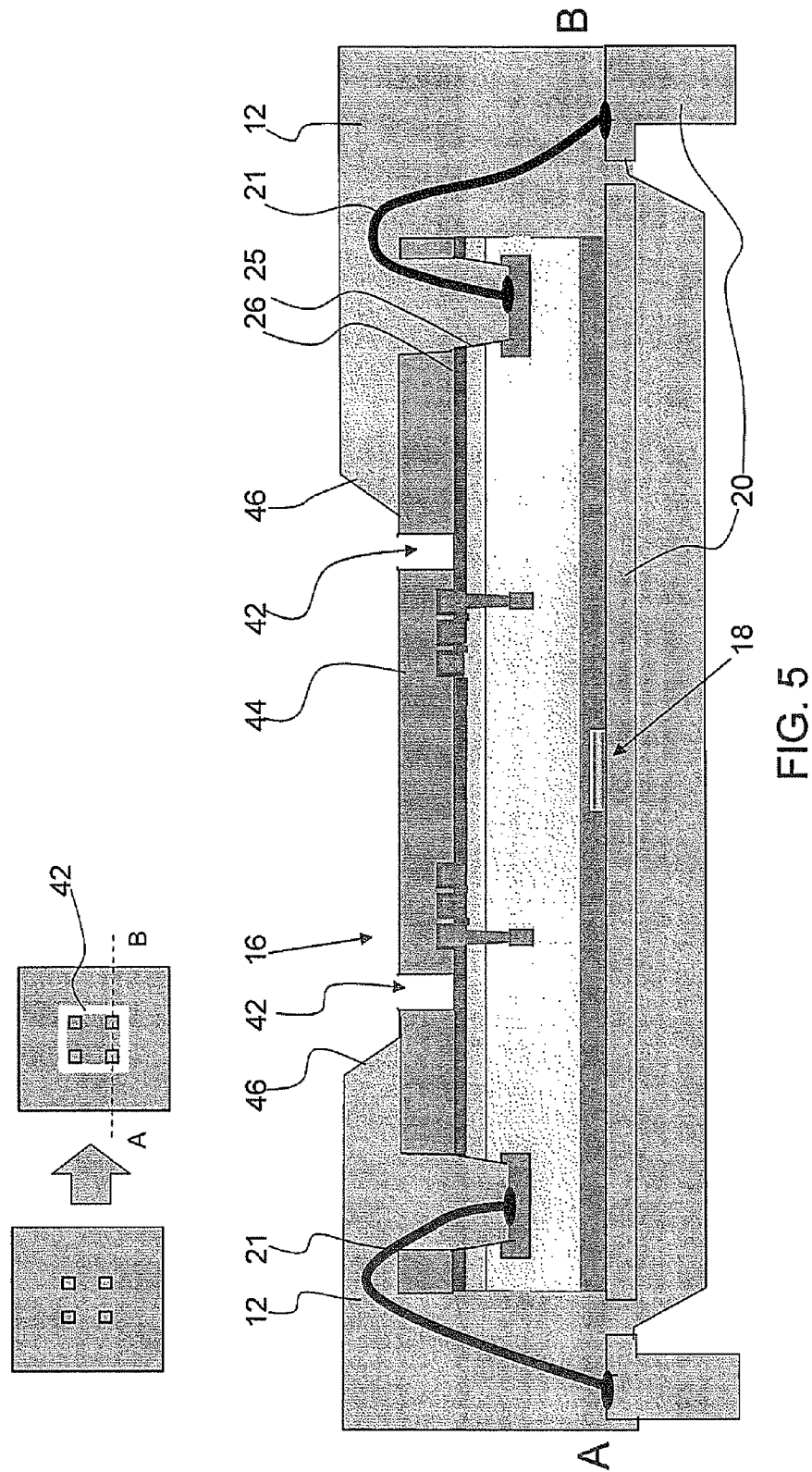
Figure 6:
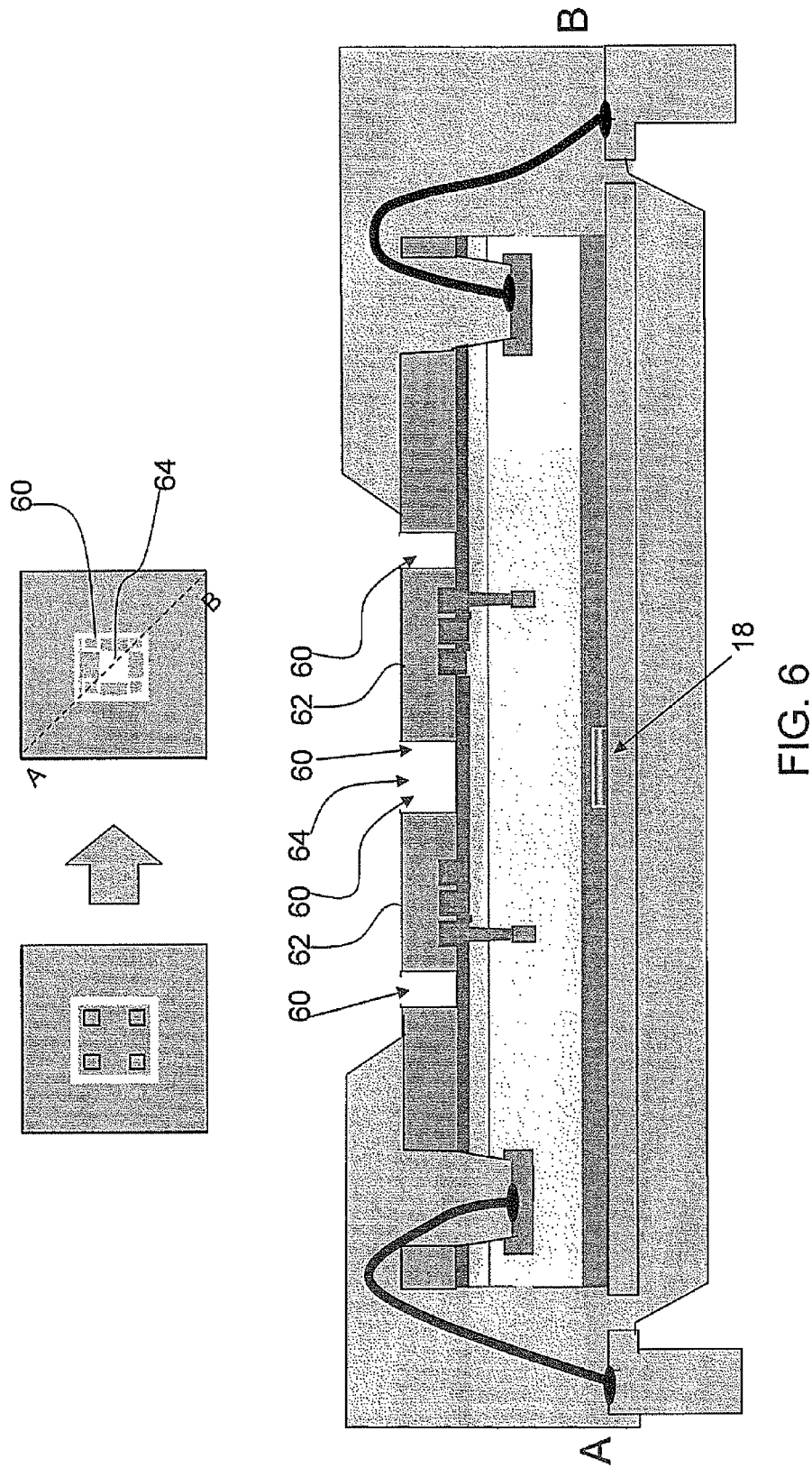
Figure 7:
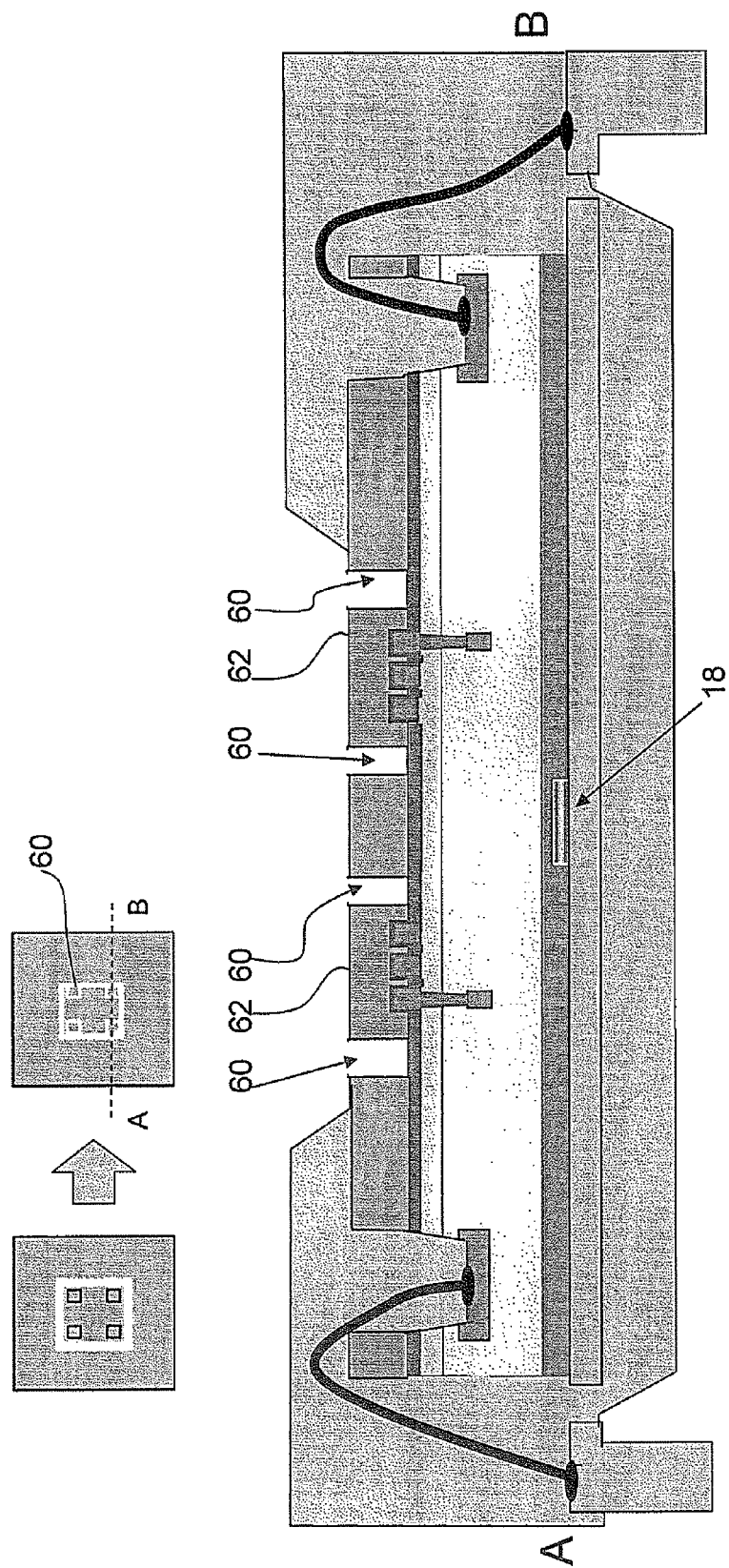

Examples of the invention are described in more detail and by way of non-limiting examples with reference to the accompanying drawings, wherein:

FIG. 1 schematically depicts a prior art IC with multiple sensors in plan view;

FIG. 2 schematically depicts the IC of FIG. 1 in cross sectional view and is used to explain the known method to manufacture the IC;

FIG. 3 is used to explain a known film assisted molding technique;

FIG. 4 schematically depicts a first example of IC with multiple sensors in cross sectional view in which the IC has been strengthened by a continuous protection layer;

FIG. 5 schematically depicts a first example of IC with multiple sensors of the invention in cross sectional view;

FIG. 6 schematically depicts a second example of IC with multiple sensors of the invention in cross sectional view; and FIG. 7 schematically depicts a third example of IC with multiple sensors of the invention in cross sectional view.

The invention provides an integrated circuit package for an integrated circuit having at least one sensor element in a sensor element area of the circuit. An encapsulation covers bond wires but leaves an opening over the sensor element area. A protection layer is provided over the integrated circuit over which the encapsulation extends, and it has a channel around the sensor element area to act as a trap for any encapsulation material which has crept into the opening area.

FIG. 1 schematically depicts a prior art IC with multiple sensors in plan view.

The circuit 10 comprises an encapsulation in the form of a molding compound 12 which covers interconnects in the form of bond wires between the integrated circuit and a lead frame. The lead frame then provides the external connections to the integrated circuit.

The encapsulation is for example a filled epoxy based molding compound.

The encapsulation has a central opening 14 so that the sensors on the top surface of the IC are exposed, and not covered by the encapsulation. The sensors are in a sensor element area. They may be at the top surface of the circuit or embedded within it, but are positioned so that they interact with the environment property being sensed, for example light or humidity. The central opening is necessary for sensors whose performance will be degraded by the presence of the encapsulation layer. There may be other sensor elements which do not need to be positioned within the central opening, so the "sensor element area" is for those sensors which benefit from not having the encapsulation layer present.

The sensors can for example comprise relative humidity sensors 16 and ambient light sensors 18, as well as gas sensors or temperature sensors (not shown) and others.

FIG. 2 schematically depicts the IC of FIG. 1 in cross sectional view and is used to explain a known method to manufacture the IC.

The carrier is shown as 20, and the bond wires 21 connect to the IC 22. The carrier can for example comprise a lead frame. The cross section of FIG. 2 schematically shows two relative humidity sensors 16 mounted on the surface of the IC, and an ambient light sensor 18 which is integrated into the structure of the IC, for example in the form of a photodiode.

The surface mounted sensors 16 connect to the top metal layer 23 of the IC, which also forms the IC bond pads, to which the bond wires 21 connect. The sensors connect to the top metal layer 23 by vias 24. These vias extend through passivation layers 25, 26 on top of the IC as well as into the IC structure to the top metal layer.

The passivation layers 25, 26 form a passivation stack, for example of $SiO_2$ (layer 25) and $Si_3N_4$ (layer 26). These layers define a high density plasma oxide and oxide planarization layer. Other layer materials may also be contemplated for the passivation stack such as $Ta_2O_5$.

In the example shown, the encapsulation 12 surrounds the IC above and below, and the carrier comprises a lead frame which defines connection points at the underside.

In this example, each humidity sensor 16 is provided with a protective cap, formed of a material through which moisture can pass, such as polyimide. This polyimide layer is removed from the area above the fully integrated ambient light sensor 18, to allow as much light as possible to reach the ambient light sensor. However, the typical thickness of the polyimide layer of around 5 μm does allow transmission of light.

FIG. 2 shows a single IC attached to a respective lead frame. In practice, many ICs will be formed on a wafer. Before encapsulation, the wafer is subjected to a back side grinding process to reduce the thickness of the resulting IC, whereas a thicker substrate is required by wafer handling equipment during the manufacturing process. FIG. 2 thus shows the IC after thinning and dicing.

The wafer grinding and dicing processes expose the IC to harsh mechanical conditions which can result in the IC cracking.

By way of example, each sensor may have dimensions of the order of 0.1 mm×0.1 mm, and each wafer sensor IC may have dimensions approximately 2 mm×2 mm. There may be thousands of sensors on each wafer, with a wafer size of around 160 mm×200 mm.

FIG. 3 is used to explain a known film assisted molding technique.

A mold 30 defines a barrier 32 which forms a closed chamber over the sensor element area. The encapsulation material 33 is pressed under the mold from the side. To prevent the encapsulation material 33 reaching the closed chamber, a large pressure (for example 120 bar) is applied to the mold so that a seal is formed, and a heated plunger 34 drives the encapsulation material 33. The heated plunger can be driven under a pressure of 60-100 bar. The pressure applied to the mold needs to be limited to avoid a risk of die breakage, and this can result in some flashing, represented by arrow 36, which can influence the sensor performance.

FIG. 4 schematically depicts a first example of IC with multiple sensors in cross sectional view in which the IC has been strengthened by a continuous protection layer. This is one possible approach considered by the applicant.

The protection layer 40 in this example covers the entire top surface of the IC apart from the bond pad locations. This provides extra resilience to the wafer grinding stresses and allows an increase in the pressure that can be applied during encapsulation molding.

The layer 40 can comprise polyimide (as previously used to cover the individual sensors).

The layer 40 has a typical thickness of 4-5 μm.

The polyimide layer can be of the photo-definable type and can be deposited by spinning and then patterned using standard lithography. Alternatively it may be formed and patterned by applying another resist and then performing an extra etching step to make the openings.

While this approach enables increased pressure to be applied during molding, the invention provides a further improvement as shown in FIG. 5.

FIG. 5 schematically depicts a first example of IC with multiple sensors of the invention in cross sectional view.

Compared to the concept in FIG. 4, the protection layer comprises a channel 42 around the sensor element area 44, which lies inside the opening 46 of the encapsulation material.

This means that any encapsulation material creeping under the mold barrier 32 (see FIG. 3) can be captured in the channel 42. The light sensor 18 can be covered by the polyimide coating 40 as shown. The channel 42 extends fully through the protection layer and can thus be formed by simple photolithographic processes.

FIG. 6 schematically depicts a second example of IC with multiple sensors of the invention in cross sectional view.

Compared to the concept in FIG. 5, the protection layer comprises a channel 60 around each sensor element which is covered by the protection layer.

In this way, a protection layer pad 62 is formed over the sensor element surrounded by a pad channel. The pad channel 60 also can extend fully through the protection layer.

This provides decoupling of the sensor elements, particularly the relative humidity sensors, to avoid any possible interference and/or drift due to diffusion of moisture or other contaminants through the polyimide protection layer.

In the example shown in FIG. 6, a central opening 64 is also provided over the ambient light sensor 18.

FIG. 7 schematically depicts a third example of IC with multiple sensors of the invention in cross sectional view.

Compared to the concept in FIG. 6, there is no central opening of the protection layer over the ambient light sensor. Instead, the protection layer comprises only the main channel around the sensor element area and the individual channels 60 around respective sensor elements.

The polyimide layer over the light sensor can be used to perform a filter function, for example it can remove the UV/blue and IR/red parts of the light spectrum.

The invention thus enables a single protection layer to be designed to reduce the risk of damage during assembly and to reduce the adverse effects of any creep of encapsulation material into a central cavity area.

The IC structure beneath the protection layer is conventional, and comprises a substrate 10 onto which a metallization stack is formed. Such a metallization stack typically comprises a stack of patterned metal layers electrically insulated from each other by electrically insulating, i.e. dielectric layers. Metal portions in different metallization layers may be conductively coupled to each other by means of vias extending through dielectric layers separating the metal portions from each other. The substrate may be any suitable substrate material, e.g. single crystal Si, SiGe, silicon on insulator and so on, and may carry a plurality of circuit elements such as transistors, diodes and others.

Equally, the metallization stack may be formed in any suitable manner, and may contain any suitable number of metal layers and dielectric layers.

Each metal layer and each dielectric layer may consist of a number of stacked sub-layers, for instance in a submicron CMOS process, stacks of Ti, TiN, AlCu, TiN may be used to define a single metal layer in the metallization stack.

Each of the dielectric layers may also comprise more than a single layer. For instance, such a dielectric layer may be a stack comprising FSG (fluorosilicate glass), $SiO_2$ and HDP oxide (High Density Plasma) any other suitable dielectric material combination. Other suitable materials may also be used.

Similarly, it will be apparent that the vias may be formed from more than a single material. For instance, in some CMOS technologies, a via may be formed by a TiN liner and a W plug. Other semiconductor processes may use different materials, e.g. Cu.

Although the described embodiments show the IC package of the present invention with a multiple environmental sensors, it will be appreciated that the concept can be applied to a single sensor, or indeed other additional sensors to those disclosed may be included in the IC design without departing from the scope of the present invention.

Polyimide is only one example of possible material to be used as the protection layer. Another example is BCB, and other examples will be apparent to those skilled in the art.

The invention has been shown for a semiconductor integrated circuit attached to a lead frame, but the invention can be applied equally to a package with the circuit attached to another carrier such as a foil, laminate or ceramic carrier.

The IC of the present invention may be integrated in any suitable electronic device, e.g. a mobile communication device such as a mobile phone, personal digital assistant and so on, or may be used as a tag for an article for monitoring purposes, in which case the IC may be extended with RF functionality, e.g. an RF transceiver communicatively coupled to the sensor(s) of the IC.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements.

Various other modifications will be apparent to those skilled in the art.

The invention claimed is:

1. An integrated circuit package, comprising:
   an integrated circuit having at least one sensor element in a sensor element area of the circuit;
   a carrier on which the integrated circuit is mounted;
   a plurality of bond wires between the integrated circuit and the carrier;
   an encapsulation which covers the bond wires and which leaves an opening over the sensor element area,
   wherein a protection layer is provided over the integrated circuit over which the encapsulation extends, wherein the protection layer comprises a channel around the sensor element area, which lies inside the opening of the encapsulation; and
   wherein the protection layer directly covers the at least one sensor element.

2. A package as claimed in claim 1, wherein the channel extends fully through the protection layer.

3. A package as claimed in claim 1, wherein each said sensor element which is covered by the protection layer comprises a protection layer pad over the sensor element surrounded by a pad channel.

4. A package as claimed in claim 3, wherein the pad channel extends fully through the protection layer.

5. A package as claimed in claim 1, wherein the protection layer comprises polyimide.

6. A package as claimed in claim 1, wherein the sensor element comprises a humidity sensor.

7. A package as claimed in claim 1, wherein the sensor element comprises an ambient light sensor.

8. A package as claimed in claim 1, wherein the channel comprises a closed shape surrounding the sensor element area.

9. A method of forming an integrated circuit package, comprising:
   providing an integrated circuit having at least one sensor element in a sensor element area of the circuit;
   mounting the integrated circuit on a carrier;
   forming a plurality of bond wires between the integrated circuit and the carrier;

forming an encapsulation layer to cover the bond wires and leave an opening over the sensor element area;

forming a protection layer over the integrated circuit before mounting on the carrier; and forming a channel in the protection layer around the sensor element area, and wherein the forming of the encapsulation layer comprises molding the encapsulation layer up to a barrier formed as part of a mold, with the channel on an inner side of the barrier.

10. A method as claimed in claim 9, wherein the encapsulation layer molding comprises film assisted molding.

11. A method as claimed in claim 9, further comprising forming the channel fully through the protection layer.

12. A method as claimed in of claim 9, further comprising covering the sensor element with the protection layer.

13. A method as claimed in claim 12, comprising, for each sensor element which is covered by the protection layer, forming a protection layer pad over the sensor element surrounded by a pad channel.

14. A method as claimed in of claim 9, wherein the protection layer comprises polyimide.

\* \* \* \* \*